(12) United States Patent
Terai (10) Patent No.: US 9,739,755 B2
(45) Date of Patent: Aug. 22, 2017

(54) FLOW RATE CONTROL MECHANISM AND GAS CHROMATOGRAPH INCLUDING FLOW RATE CONTROL MECHANISM

(71) Applicant: SHIMADZU CORPORATION, Kyoto-shi, Kyoto (JP)

(72) Inventor: Yasunori Terai, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 477 days.

(21) Appl. No.: 14/287,753

(22) Filed: May 27, 2014

(65) Prior Publication Data
US 2015/0346167 A1   Dec. 3, 2015

(51) Int. Cl.
| | |
|---|---|
| G01N 30/32 | (2006.01) |
| G01N 30/10 | (2006.01) |
| G01N 30/16 | (2006.01) |
| F16K 7/02 | (2006.01) |
| G01N 30/68 | (2006.01) |
| G01N 30/02 | (2006.01) |

(52) U.S. Cl.
CPC ............... *G01N 30/32* (2013.01); *F16K 7/02* (2013.01); *G01N 30/10* (2013.01); *G01N 30/16* (2013.01); *G01N 30/68* (2013.01); *G01N 2030/025* (2013.01); *G01N 2030/324* (2013.01)

(58) Field of Classification Search
CPC ....... G01N 2030/025; G01N 2030/324; G01N 30/10; G01N 30/16; G01N 30/32; G01N 30/68; F16K 7/02
See application file for complete search history.

(56) References Cited

U.S. PATENT DOCUMENTS 3,289,999 A * 12/1966 Konzak ............... A61M 39/285
                                                       24/134 R
3,335,753 A *  8/1967 Kiser ................... B67D 3/0003
                                                       128/DIG. 13
(Continued)

FOREIGN PATENT DOCUMENTS

| CN | 1643466 A | 7/2005 |
|---|---|---|
| JP | H05126663 | 5/1993 |

(Continued)

OTHER PUBLICATIONS

Eren, H. 1999. Flowmeters. Wiley Encyclopedia of Electrical and Electronics Engineering.*

(Continued)

*Primary Examiner* — Lisa Caputo
*Assistant Examiner* — Punam Roy
(74) *Attorney, Agent, or Firm* — Sughrue Mion, PLLC (57) ABSTRACT

One end of carrier gas channel, purge gas channel and split gas channel is connected to sample gasification chamber. The other end of carrier gas channel, purge gas channel, and split gas channel is connected to a flow rate control mechanism in the form of carrier gas flow rate control block, purge gas flow rate control block and split gas flow rate control block respectively. Carrier gas flow rate control block, purge gas flow rate control block and split gas flow rate control block constitute a flow rate control unit. This reduces the possibility of leakage of gas to the outside and admixture of impurities from the outside in the flow rate control mechanism.

6 Claims, 6 Drawing Sheets (56) References Cited

U.S. PATENT DOCUMENTS

| | | | | |
|---|---|---|---|---|
| 3,893,477 | A * | 7/1975 | Stoll | F16K 15/183 |
| | | | | 137/599.11 |
| 4,100,803 | A * | 7/1978 | Gass | G01F 1/08 |
| | | | | 73/861.81 |
| 5,326,033 | A * | 7/1994 | Anfindsen | F16K 7/065 |
| | | | | 239/300 |
| 6,708,944 | B2 * | 3/2004 | Pfeil | A61M 5/16881 |
| | | | | 251/6 |
| 2008/0264863 | A1 * | 10/2008 | Quake | B01J 20/286 |
| | | | | 210/651 |

FOREIGN PATENT DOCUMENTS

| | | |
|---|---|---|
| JP | H08-000769 | 5/1996 |
| JP | H11-311359 | 11/1999 |
| JP | 2000-019165 A | 1/2000 |
| JP | 2003-232462 | 8/2003 |
| JP | 2008-064542 | 3/2008 |
| JP | 2008-190942 | 8/2008 |
| JP | 2009-288210 A | 12/2009 |

OTHER PUBLICATIONS

Chinese Office Action issued Jun. 10, 2014 in Chinese Patent Application No. 201210359317.5.

* cited by examiner

FIG. 6
RELATED ART

FLOW RATE CONTROL MECHANISM AND GAS CHROMATOGRAPH INCLUDING FLOW RATE CONTROL MECHANISM

This application incorporates by reference Japan Patent Publication No. 2013-124673, published Jun. 24, 2013 to the same inventors.

TECHNICAL FIELD

The present invention relates to a flow rate control mechanism which is interposed between a gas supply source and a gas channel which guides the gas to a predetermined part, in order to control the gas flow rate; the invention also relates to a gas chromatograph comprising said flow rate control mechanism.

BACKGROUND ART

Gas chromatographs comprise an analytical column, a sample introduction channel for guiding the sample to the analytical column, a sample injection unit for injecting the sample into the sample introduction channel, a carrier gas supply unit for supplying carrier gas to the sample injection unit, and a detector (for example, see Patent literature 1). The sample is injected from the sample introduction unit and is conveyed to the analytical column by the carrier gas supplied from the carrier gas supply unit and separated in the analytical column, and the components thereof are detected in the detector provided downstream of the analytical column.

In this sort of gas chromatograph, in order to adjust the carrier gas supply rate from the bottle, a flow controller (flow rate control mechanism) is employed, comprising devices such as a flow rate control valve, pressure sensor, flow rate sensor, etc. mounted on a channel substrate inside which channels are provided.

Figure 5:
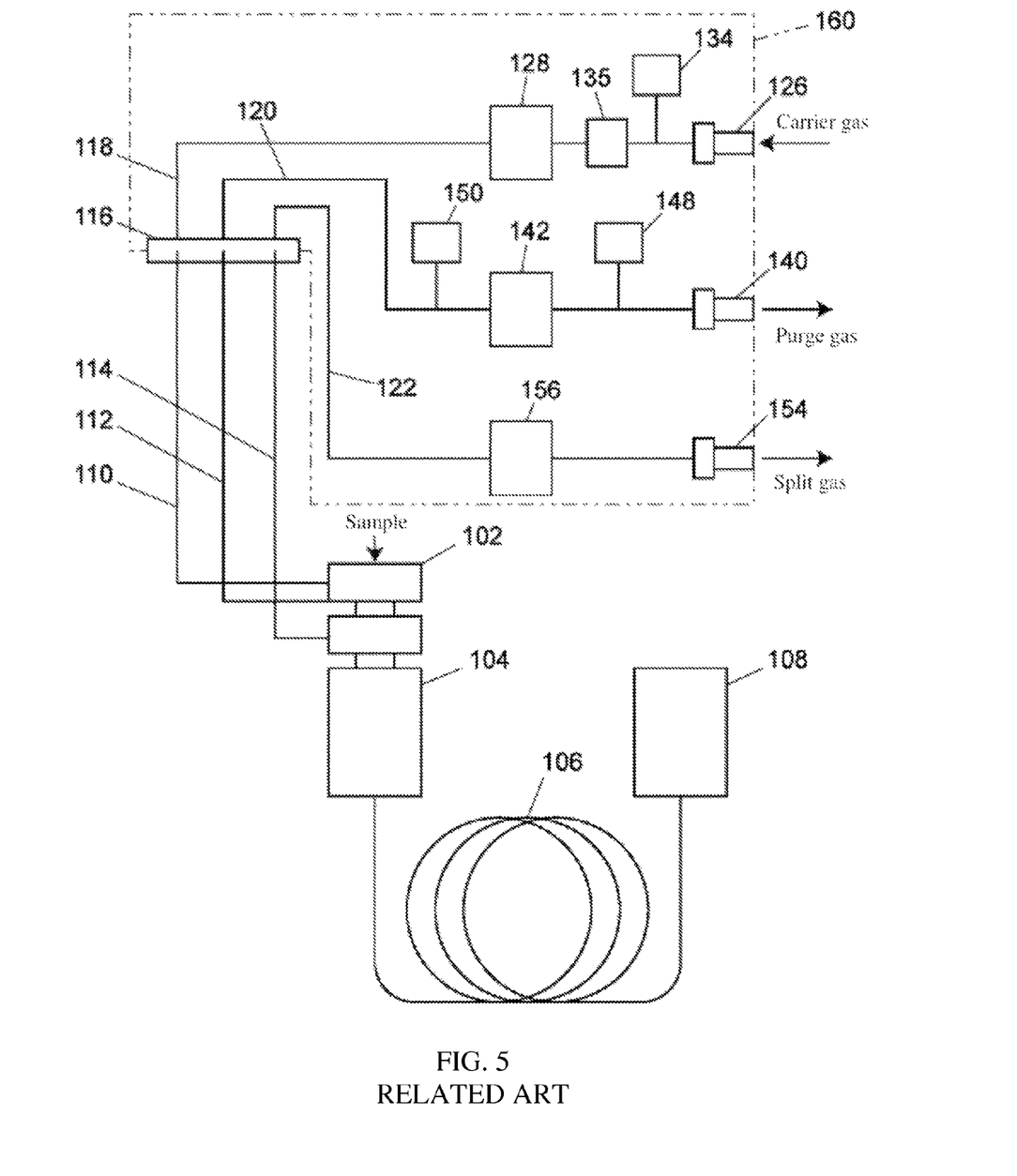
FIG. 5 is a channel diagram showing an example of a conventional gas chromatograph.

The channel configuration of a conventional gas chromatograph will be explained using FIG. 5.

One end of carrier gas channel 110, purge gas channel 112 and split gas channel 114 is connected to pipe connection unit 116 provided in flow rate control unit 160. The other end of carrier gas channel 110, purge gas channel 112 and split gas channel 114 is connected to sample introduction unit 102. Carrier gas channel 110 is a pipe for introducing carrier gas into sample introduction unit 102; purge gas channel 112 is a pipe for discharging purge gas for purging the inside of the sample introduction unit 102; and split gas channel 114 is a pipe for discharging sample and carrier gas which are not introduced into analytical column 106. It will be noted that a portion of the carrier gas is used as sparge gas.

Flow rate control unit 160 comprises channels 118, 120 and 122, and one end of these channels 118, 120 and 122 is connected to pipe connection unit 116. The other end of channels 118, 120 and 122 is connected respectively to pipe connection units 126, 140 and 154. A pipe communicating with a bottle for supplying carrier gas is connected to pipe connection unit 126, a pipe for discharging purge gas to the outside is connected to pipe connection unit 140, and a pipe for discharging split gas to the outside is connected to pipe connection unit 154.

In channel 118, from the pipe connection unit 126 side, there is provided a pressure sensor 134, flow rate sensor 135 and flow rate control valve 128. In channel 120, from the pipe connection unit 140 side, there is provided a pressure sensor 148, flow rate control valve 142 and pressure sensor 150. In channel 122, there is provided a flow rate control valve 156.

Figure 6:
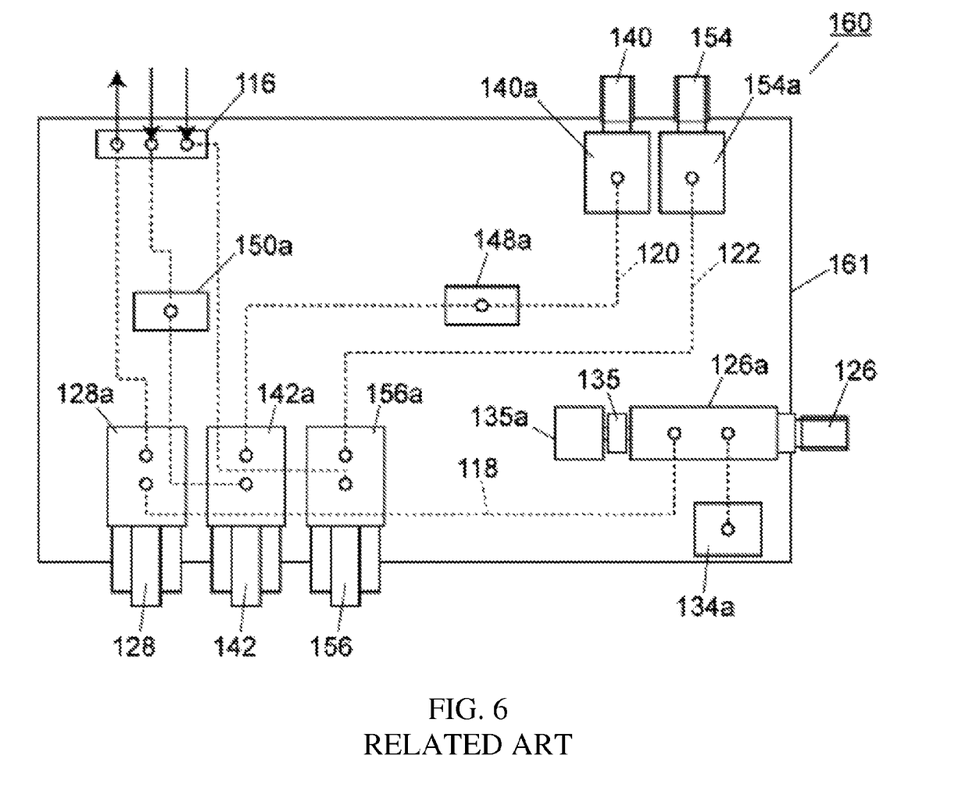
FIG. 6 is a plan view showing an example of a conventional flow rate control mechanism of a gas chromatograph using a channel substrate.

This flow rate control unit 160, as shown in FIG. 6, can be configured using a channel substrate 161 inside which channels are formed. In the example of FIG. 6, internal channels, i.e. channels 118, 120 and 122 are provided inside the channel substrate 161, holes communicating with each channel are provided on the surface, a connection block is interposed at the locations of those holes, and a pipe connection unit, pressure sensor, flow rate sensor, flow rate control valve, etc. are mounted by means of the connection blocks. The channel connection part of each element is sealed using an O-ring made of fluorine rubber, etc. in order to maintain air-tightness.

PRIOR ART LITERATURES (Patent literature 1) Japanese Unexamined Patent Application Publication 2000-19165

SUMMARY OF THE INVENTION

In the conventional gas flow rate control mechanism of gas chromatographs, as described above, many component elements such as a pipe connection unit, pressure sensor, flow rate sensor, flow rate control valve, connection block, etc., are connected to a channel, so there are many channel connections. While air-tightness of the connections between component parts and channels is maintained with O-rings made of fluorine rubber or the like, there is the possibility that the gas which is inside will leak from these connections, or that outside air or impurities will become admixed into the channels. If even if a trace amount of outside air or impurities should become admixed into the channels of a gas chromatograph, it is possible that the analysis results of the gas chromatograph will be affected. This risk becomes higher, the greater the number of component parts connected to the channels.

It is therefore an object of the present invention to reduce the possibility of leakage of gas to the outside and admixture of impurities from the outside in a flow rate control mechanism which controls the flow rate of gas.

MEANS FOR SOLVING THE PROBLEM

The flow rate control mechanism pertaining to the present invention comprises a single block in which are integrally joined: a first connection unit for connecting a gas supply source which supplies gas; a second connection unit for connecting a gas channel for guiding gas from the gas supply source to a predetermined part; an internal channel which connects the first connection unit to the second connection unit; and a flow rate control valve which controls the flow rate of gas flowing between the first connection unit and second connection unit by adjusting the channel width of the internal channel.

In the prior art, in order to construct a flow rate control mechanism which controls the supply rate of gas from a gas supply source to a gas channel, it is necessary to create the connections: gas supply source-connection block-channel-connection block-flow rate control valve-connection block-channel-gas channel. Thus, there were many channel connection parts using a sealing member such as an O-ring.

By contrast, the flow rate control mechanism pertaining to the present invention comprises a single block in which are integrally joined: a first connection unit for connecting a gas supply source; a second connection unit for connecting a gas channel; an internal channel which connects the first connection unit to the second connection unit; and a flow rate control valve which controls the flow rate of gas flowing between the first connection unit and second connection unit. Therefore, the flow rate control mechanism which controls the supply rate of gas from the gas supply source to the gas channel can be implemented with a simple configuration of carrier gas supply unit-flow rate control block-gas channel, making it possible to greatly reduce the channel connection parts using a sealing member such as an O-ring.

The first gas chromatograph pertaining to the present invention comprises an analytical column for separating a sample; a detector for detecting the sample separated in the analytical column; a sample introduction channel for guiding the sample to the analytical column; a sample injection unit for injecting the sample into the sample introduction channel; and a carrier gas supply unit which supplies, to the sample injection unit, a carrier gas for conveying, to the analytical column, the sample injected from the sample injection unit; and is characterized in that a flow rate control mechanism of the present invention is interposed between a carrier gas supply source and a channel of the carrier gas supply unit which communicates with the sample injection unit.

The flow rate control mechanism which controls the flow rate of carrier gas is fashioned as a single block, so the number of channel connection parts to be sealed with O-rings is greatly reduced.

The second gas chromatograph pertaining to the present invention is characterized in that the flow rate control mechanism of the present invention is interposed between the detector gas supply source and a channel of the detector gas supply unit for supplying detector gas to the detector, which channel communicates with the detector. Just as in the case of the flow rate control mechanism which controls the supply rate of carrier gas of the first gas chromatograph described above, the flow rate control mechanism which controls the supply rate of detector gas here is fashioned as a single block, so the number of channel connection parts to be sealed with an O-ring is greatly reduced.

The flow rate control mechanism of the present invention comprises a single block in which are integrally joined: a first connection unit for connecting a gas supply source; a second connection unit for connecting a gas channel; an internal channel which connects the first connection unit to the second connection unit; and a flow rate control valve which controls the flow rate of gas flowing between the first connection unit and second connection unit; thus, the flow rate control mechanism which controls the supply rate of gas from the gas supply source to the gas channel can be implemented with a simple channel configuration of carrier gas supply unit-flow rate control block-gas channel, making it possible to greatly reduce the number of channel connection parts using a sealing member such as an O-ring. It is thereby possible to reduce the risk of leakage of gas to the outside and admixture of gas and impurities from the outside in the flow rate control mechanism.

DETAILED DESCRIPTION OF THE EXEMPLARY EMBODIMENTS

In a preferable example of embodiment of the present invention, within the block, there is further provided a sensor connection channel whereof one end communicates with the internal channel and which serves for connecting a pressure sensor to the internal channel. Conventionally, when connecting a pressure sensor to a channel through which gas flows, it was necessary to connect the pressure sensor via a connection block to the channel through which gas flows, so the number of channel connection parts using a sealing member such as an O-ring would further increase. By contrast, by making it possible to directly connect the pressure sensor to the block of the flow rate control mechanism of the present invention by providing a channel for connecting the pressure sensor, the increase in the number of channel connection parts using a sealing member such as an O-ring can be kept to a minimum.

Figure 1:
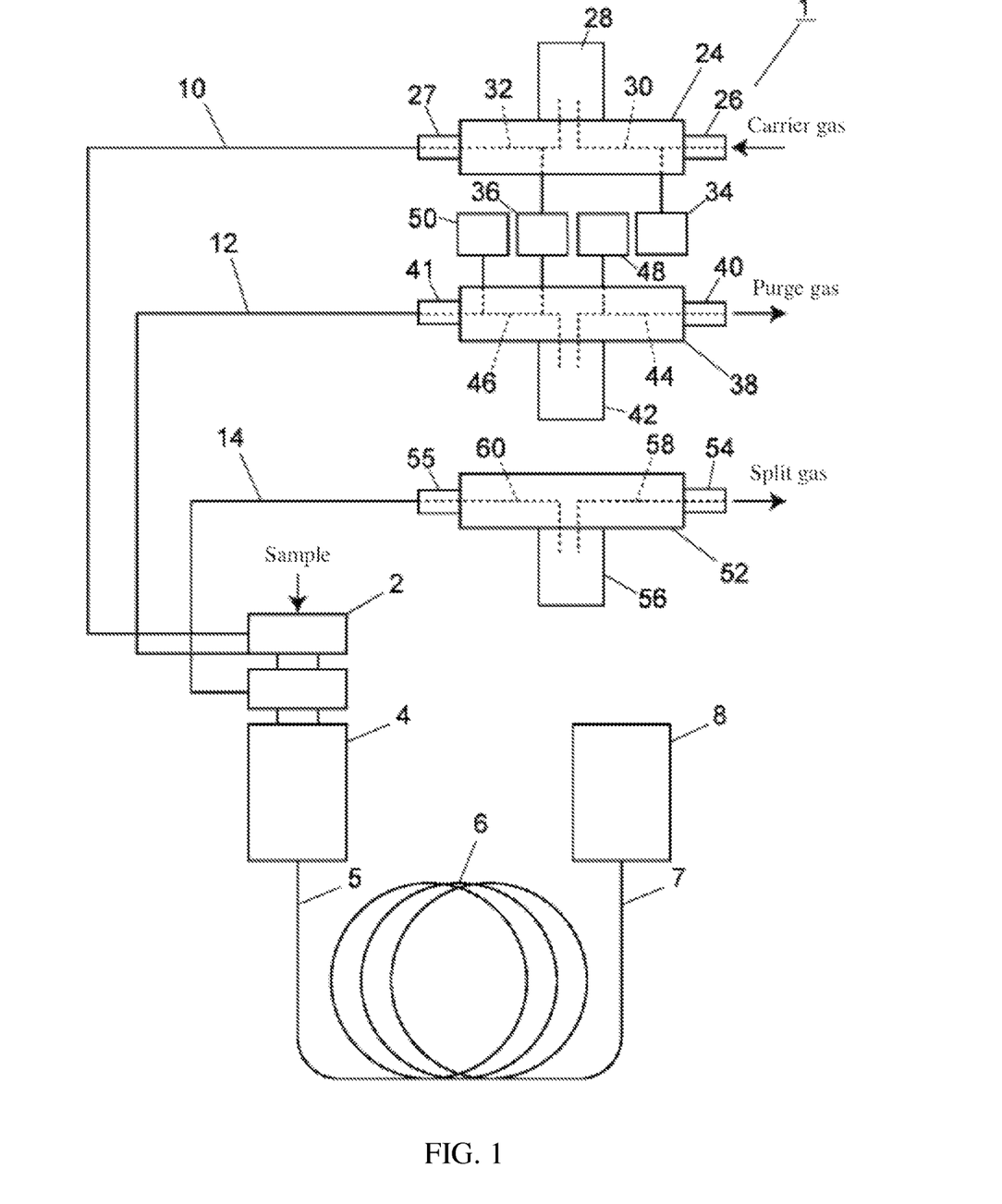
FIG. 1 is a channel diagram showing an example of embodiment of a gas chromatograph.

An example of embodiment of a gas chromatograph will be described below using FIG. 1.

This gas chromatograph comprises a flow rate control unit 1, sample gasification chamber 4, sample introduction channel 5, analytical column 6, detection channel 7 and detector 8.

One end of carrier gas channel 10, purge gas channel 12 and split gas channel 14 is connected to sample gasification chamber 4. The other end of carrier gas channel 10, purge gas channel 12 and split gas channel 14 is connected respectively to a flow rate control mechanism in the form of carrier gas flow rate control block 24, purge gas flow rate control block 40 and split gas flow rate control block 52. Carrier gas flow rate control block 24, purge gas flow rate control block 40 and split gas flow rate control block 52 constitute a flow rate control unit 1.

Figure 3:
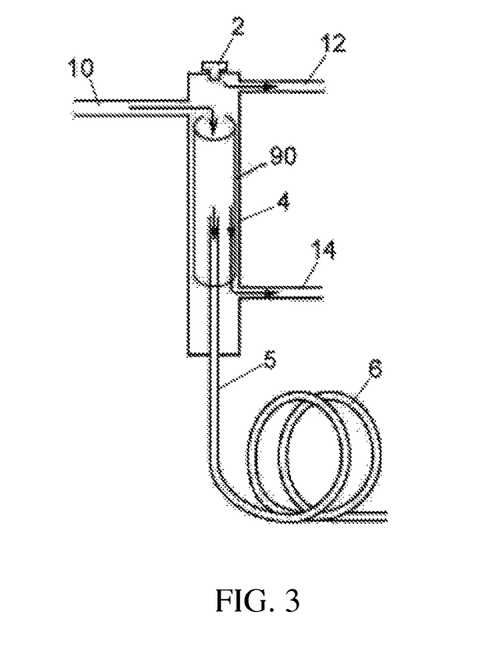
FIG. 3 is a cross-sectional view showing an example of the structure of a sample introduction unit and sample gasification chamber.

A sample injection unit 2 is provided in the top of sample gasification chamber 4. In sample gasification chamber 4, as shown in FIG. 3, a portion of the carrier gas supplied through carrier gas channel 10 conveys the sample injected from sample injection unit 2 towards insert unit 90, and the rest of the carrier gas passes as purge gas through purge gas channel 12 and is discharged to the outside. A portion of the gas containing gasified sample (hereinafter, sample gas), conveyed toward the insert 90, passes through sample introduction channel 5 and is guided to analytical column 6, while the rest of the sample gas passes as split gas through split gas channel 14 and is discharged to the outside. Gas containing components separated in analytical column 6 passes through detection channel 7 and is guided to detector 8 to undergo detection.

Carrier gas flow rate control block 24 comprises a flow rate control valve 28 which controls the flow rate of carrier gas flowing between internal channels 30-32 by adjusting the width of the channel connecting one end of internal channel 30 and one end of internal channel 32. The other end of channel 30 communicates with a first channel connection part in the form of pipe connection unit 26 for connecting a carrier gas bottle, and the other end of channel 32 communicates with a second channel connection unit in the form of pipe connection unit 27 to which is connected a carrier gas channel 10 leading to sample introduction unit 2. Pressure sensor 34 is connected to internal channel 30 and differential pressure sensor 36 is connected to internal channel 32. Differential pressure sensor 36 is also connected to internal channel 46 of purge gas flow rate control block 38 and measures the differential pressure between the two channels 32 and 46.

Purge gas flow rate control block 38 comprises a flow rate control valve 42 which controls the flow rate of purge gas flowing between internal channels 46-44 by adjusting the width of the channel connecting one end of internal channel 44 to one end of internal channel 46. The other end of channel 44 communicates with pipe connection unit 40 for connecting a purge gas discharge channel, and the other end of channel 46 communicates with pipe connection unit 41 for connecting purge gas channel 12, which leads to sample introduction unit 2. Pressure sensor 48 is connected to internal channel 44, and differential pressure sensor 36 and pressure sensor 50 are connected to internal channel 46.

Split gas flow rate control block 52 comprises a flow rate control valve 56 which controls the flow rate of split gas flowing between internal channels 60-58 by adjusting the width of the channel connecting one end of internal channel 58 and one end of internal channel 60. The other end of internal channel 58 communicates with pipe connection unit 54, and the other end of internal channel 60 communicates with pipe connection unit 55 for connecting split gas channel 14 which leads to sample introduction unit 2.

Figure 2:
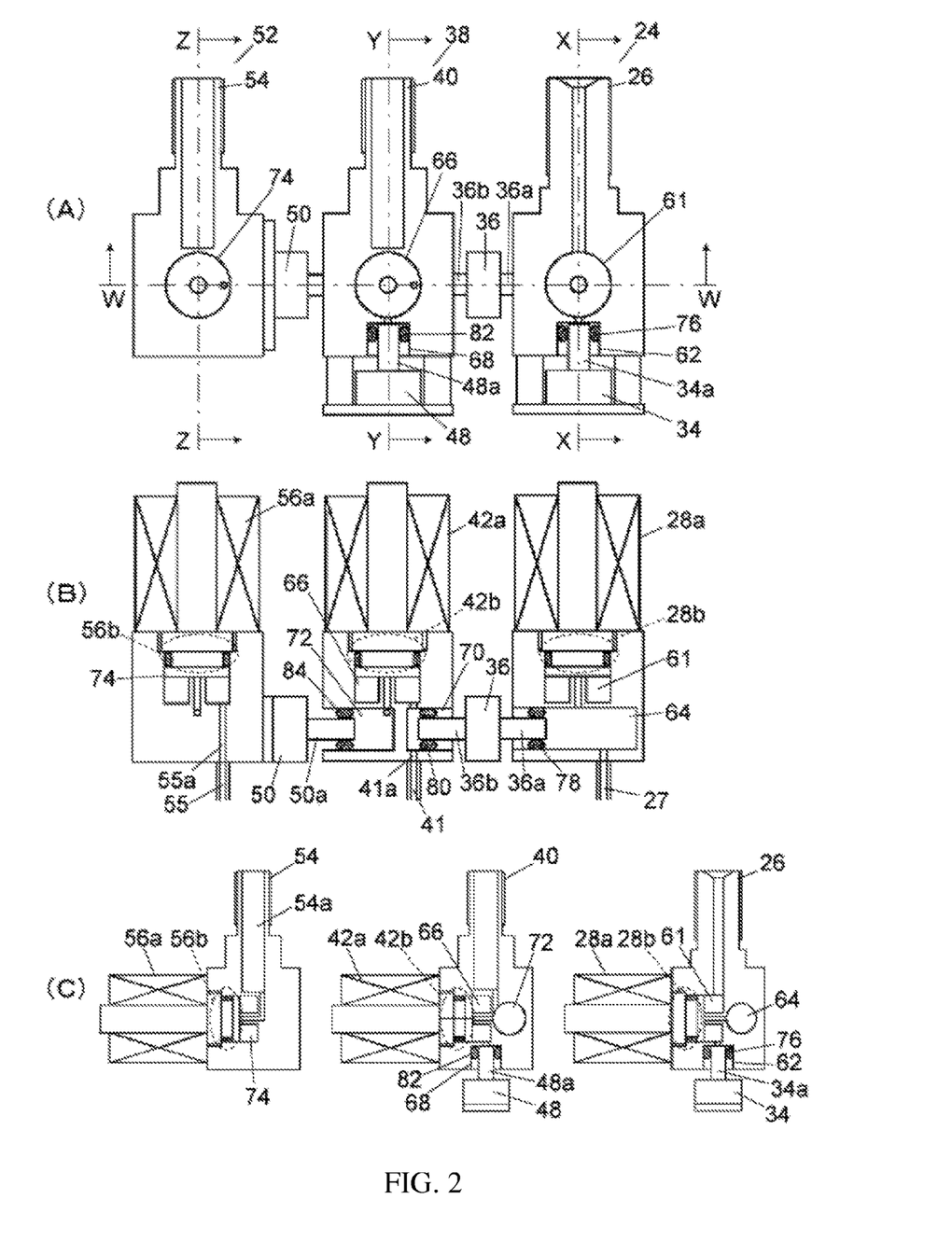
FIG. 2 is a diagram showing an example of the structure of various flow rate control blocks of a flow rate control unit, where (A) is a front cross-sectional view, (B) is a cross-sectional view at the location W-W of (A), and (C) is a cross-sectional view at the location X-X, location Y-Y and location Z-Z of (A).

The cross-sectional structure of carrier gas flow rate control block 24, purge gas flow rate control block 38 and split gas flow rate control block 52 is shown in FIG. 2. FIG. 2 (B) shows the cross-section of position W-W of (A), and (C) shows the cross-section at position X-X of carrier gas flow rate control block 24, position Y-Y of purge gas flow rate control block 38 and position Z-Z of split gas flow rate control block 52.

First, the carrier gas flow rate control block 24 will be described.

Hollow parts 61, 62 and 64 are provided inside the carrier gas flow rate control block 24. Hollow part 61 communicates via a channel with pipe connection unit 26. Hollow part 61 communicates via a channel with hollow part 62. The tip of pipe 34a of pressure sensor 34 is inserted into hollow part 62 and is connected to the channel which communicates with hollow part 61. The connection part between pipe 34a and the channel communicating with hollow part 61 is sealed with an O-ring 76. Pressure sensor 34 is thereby connected to hollow part 61. Pressure sensor 34 is supported by a member provided on carrier gas flow rate control block 24, and is integrally joined with carrier gas flow rate control block 24.

Hollow part 64 communicates via a channel with pipe connection unit 27. Furthermore, the tip of pipe 36a of differential pressure sensor 36 is inserted into hollow part 64, and the gap between the outer circumference of pipe 36a and the inner circumference of hollow part 64 is sealed with an O-ring 78. Differential pressure sensor 36 is thus connected to hollow part 64.

Hollow part 61 and hollow part 64 both communicate with flow rate adjustment unit 28b. Flow rate adjustment unit 28b adjusts the flow rate of carrier gas flowing from hollow part 61 to hollow part 64 by adjusting the width of the channel connecting hollow part 61 to hollow part 64 by means of a diaphragm of valve driving unit 28a. The supply rate of carrier gas from a carrier gas bottle connected to pipe connection unit 26 is adjusted in this way.

Next, the purge gas flow rate control block 38 will be described.

Hollow parts 66, 68, 70 and 72 are provided inside the purge gas flow rate control block 38. Hollow part 66 and hollow part 68 communicate via a channel, and hollow part 66 and hollow part 70 also communicate via a channel. The tip of pipe 48a of pressure sensor 48 is inserted into hollow part 68, and pipe 48a is connected to one end of the channel at the rear wall of hollow part 68 which communicates with hollow part 66. The connection area between pipe 48a and the channel which communicates with hollow part 66 is sealed by means of an O-ring 82. Pressure sensor 48 is thus connected to hollow part 66. Pressure sensor 48 is retained by a member provided on the purge gas flow rate control block 38 and is integrally joined with the purge gas flow rate control block 38.

Pipe connection unit 41 is connected via a channel to hollow part 70. Furthermore, the tip of pipe 36b of differential pressure sensor 36 is inserted into hollow part 70, and the gap between the outer circumference of pipe 36b and the inner circumference of hollow part 70 is sealed with an O-ring 80. In this way, the differential pressure sensor 36 is connected inside the hollow part 70.

Hollow part 72 communicates with pipe connection part 40 via a channel. Furthermore, the tip of pipe 50a of pressure sensor 50 is inserted into hollow part 72, and the gap between the outer circumference of pipe 50a and the inner circumference of hollow part 72 is sealed by O-ring 84. In this way, the pressure sensor 50 is connected inside hollow part 72. Pressure sensor 50 is secured to split gas flow rate control block 54.

Hollow part 66 and hollow part 72 communicate with flow rate adjustment part 42b. Flow rate adjustment unit 42b adjusts the flow rate of purge gas flowing from hollow part 66 to hollow part 72 by adjusting the width of the channel connecting hollow part 66 and hollow part 72 by means of the diaphragm of valve driving unit 42a. The purge gas flow rate from pipe connection unit 40 is adjusted in this manner.

Next, the split gas flow rate control block 52 will be described.

A hollow part 74 is provided inside the split gas flow rate control block 52. Pipe connection unit 55 is connected via channel 55a to hollow part 74. Hollow part 74 communicates with flow rate adjustment unit 56b, and pipe connection unit 54 is also connected via a channel to flow rate adjustment unit 56b. Flow rate adjustment unit 56b adjusts the flow rate of split gas flowing from hollow part 74 to pipe connection unit 54 by adjusting the width of the channel connecting hollow part 74 and pipe connection unit 54 by means of a diaphragm of valve driving part 56a. The split gas flow rate from pipe connection unit 54 is adjusted in this manner.

Based on the above configuration of blocks 24, 38 and 52, all the channels from inlet to outlet for carrier gas, purge gas or split gas are fashioned within a single block, and the valve mechanism which adjusts the flow rate of the gas passing through those channels is also provided within the same block, so the places which need to be sealed using an O-ring are limited to the connection locations of the pressure sensor and differential pressure sensor, allowing the structure of the flow rate control unit 1 comprising these blocks 24, 38 and 52 to be made into a structure with a low possibility of outflow of gas to the outside and admixture of gas or impurities from the outside.

Employing this sort of structure eliminates the need for a channel substrate on which components such as valves and connecting members are mounted and connected via internal channels. As a result, the problem of air-tightness at the connection areas of these components to the channel substrate is eliminated. Furthermore, since the channel substrate and parts such as connection blocks for connecting the components to the channel substrate become unnecessary, the number of component parts is reduced and costs can be decreased.

Figure 4:
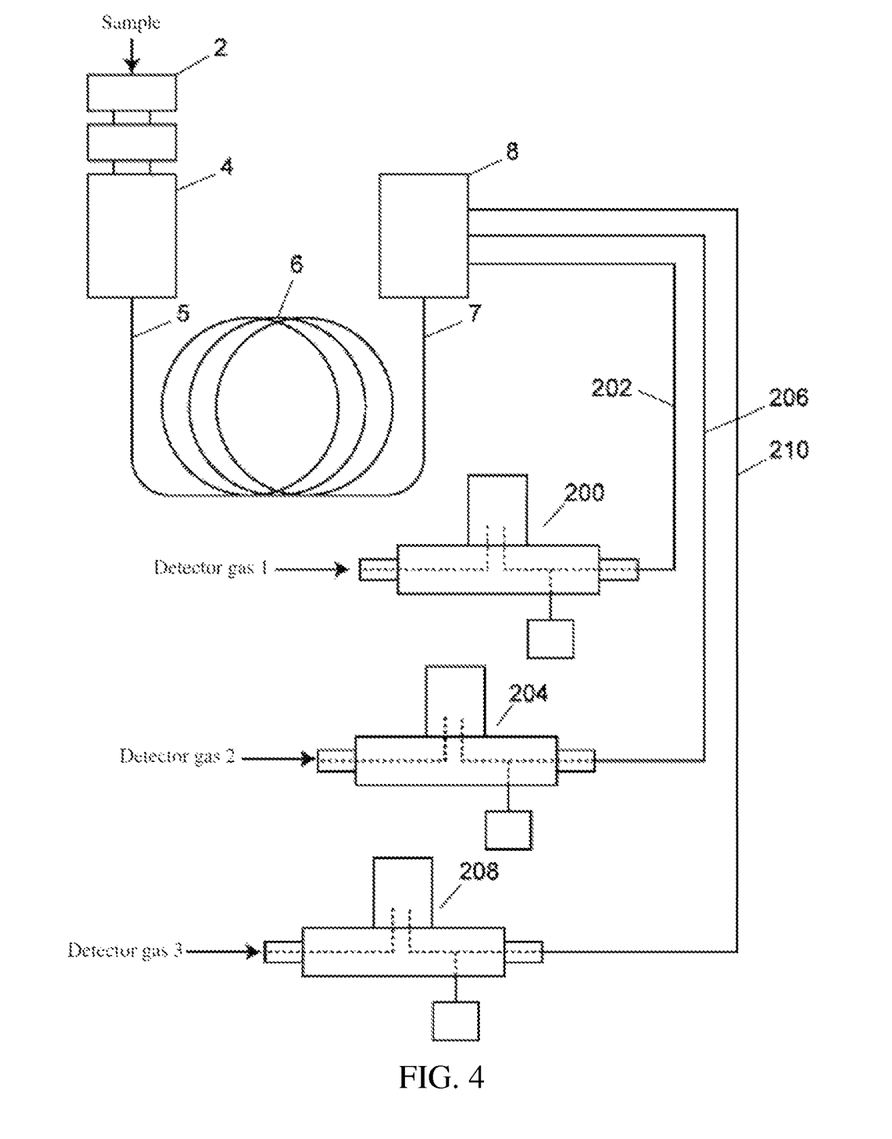
FIG. 4 is a channel diagram showing an example of embodiment of a detector gas flow rate control unit.

Furthermore, gas, which is required in principle, is supplied to the detector 8. If the detector 8 is, for example, a hydrogen flame ionization detector (FID), it is necessary to supply at least hydrogen and air as the detector gas to the detector 8. FIG. 4 is an example of the channel configuration for supplying detector gas to detector 8, and in this example, as the flow rate control mechanism which controls the supply rate of detector gas to the detector 8, flow rate control blocks 200, 204 and 208 having an equivalent structure to carrier gas flow rate control block 24 are interposed in channels 202, 206 and 210 which communicate with the detector gas supply sources and detector 8. Examples of detector gas include, for instance, hydrogen as detector gas 1, air as detector gas 2 and nitrogen or helium as detector gas 3.

In this way, it is possible to use a flow rate control mechanism (flow rate control block) consisting of a single block not just as a carrier gas flow rate control unit but also in other places where gas flow rate needs to be controlled. It is thereby possible to prevent outflow of gas to the outside and admixture of foreign substances from the outside and to simplify the device configuration.

DESCRIPTION OF REFERENCES

1 Flow rate control mechanism
2 Sample injection unit
4 Sample gasification chamber
5 Sample introduction channel
6 Analytical column
7 Detection channel
8 Detector
10 Carrier gas channel
12 Purge gas channel
14 Split gas channel
24 Carrier gas flow rate control block
26, 27, 40, 41, 54, 55 Pipe connection unit
28, 42, 56 Flow rate control valve
30, 32, 44, 46, 58, 60 Channel (within block)
34, 48, 50 Pressure sensor
36 Differential pressure sensor

What is claimed is:

1. A gas chromatograph apparatus comprising:
a flow rate control mechanism comprising a single block in which are integrally joined:
a first connection unit for connecting a gas supply source which supplies gas;
a second connection unit for connecting a gas channel for guiding gas from said gas supply source to a predetermined part;
an internal channel which connects said first connection unit to said second connection unit; and
a flow rate control valve which controls the flow rate of gas flowing between said first connection unit and said second connection unit by adjusting the channel width of said internal channel;
analytical column for separating a sample;
detector for detecting the sample which has been separated in said analytical column;
sample introduction channel for guiding the sample into said analytical column;
sample injection unit for injecting the sample into said sample introduction channel; and
carrier gas supply unit which supplies a carrier gas to the sample injection unit for conveying the sample injected from the sample injection unit toward the analytical column, wherein
the flow rate control mechanism is interposed between the carrier gas supply source and the channel of said carrier gas supply unit which communicates with the sample injection unit.

2. The gas chromatograph apparatus as described in claim 1, further comprising, within said block, a sensor connection channel for connecting a pressure sensor to said internal channel, one end of which second channel communicates with said internal channel.

3. The gas chromatograph apparatus as described in claim 2, wherein said block integrally retains said pressure sensor.

4. A gas chromatograph apparatus comprising:
a flow rate control mechanism comprising a single block in which are integrally joined:
a first connection unit for connecting a gas supply source which supplies gas;
a second connection unit for connecting a gas channel for guiding gas from said gas supply source to a predetermined part;
an internal channel which connects said first connection unit to said second connection unit; and
a flow rate control valve which controls the flow rate of gas flowing between said first connection unit and said second connection unit by adjusting the channel width of said internal channel;
an analytical column for separating a sample,
a detector for detecting the sample which has been separated in said analytical column,
a sample introduction channel for guiding the sample into said analytical column,
a sample injection unit for injecting the sample into said sample introduction channel,
a carrier gas supply unit which supplies a carrier gas to said sample injection unit for conveying the sample injected from said sample injection unit toward said analytical column,
a detector gas supply unit for supplying detector gas to said detector, and
the flow rate control mechanism interposed between the detector gas supply source and the channel of said detector gas supply unit which communicates with said detector.

5. The gas chromatograph of claim 4, further comprising, within said block, a sensor connection channel for connecting a pressure sensor to said internal channel, one end of which second channel communicates with said internal channel.

6. The gas chromatograph of claim 5, wherein said block integrally retains said pressure sensor.

* * * * *